United States Patent
Roth et al.

(10) Patent No.: US 11,104,665 B2
(45) Date of Patent: Aug. 31, 2021

(54) PYRIDAZINES

(71) Applicant: Boehringer Ingelheim International GmbH, Ingelheim am Rhein (DE)

(72) Inventors: Gerald Juergen Roth, Warthausen (DE); Tom Bretschneider, Biberach an der Riss (DE); Christian Andreas Kuttruff, Warthausen (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 16/663,492

(22) Filed: Oct. 25, 2019

(65) Prior Publication Data

US 2020/0131151 A1 Apr. 30, 2020

(30) Foreign Application Priority Data

Oct. 29, 2018 (EP) .................................. 18203226

(51) Int. Cl.
*C07D 237/22* (2006.01)
*C07D 401/12* (2006.01)
*C07D 401/14* (2006.01)
*C07D 403/12* (2006.01)

(52) U.S. Cl.
CPC ......... *C07D 401/14* (2013.01); *C07D 403/12* (2013.01)

(58) Field of Classification Search
CPC ... C07D 401/12; C07D 401/14; C07D 237/22
See application file for complete search history.

(56) References Cited

U.S. PATENT DOCUMENTS

| | | |
|---|---|---|
| 2016/0287584 A1 | 10/2016 | Gibson et al. |
| 2018/0127425 A1 | 5/2018 | Desroy et al. |
| 2021/0024492 A1 | 1/2021 | Kuttruff et al. |
| 2021/0024495 A1 | 1/2021 | Kuttruff et al. |

FOREIGN PATENT DOCUMENTS

| | | |
|---|---|---|
| WO | 2014139882 A1 | 9/2014 |
| WO | 2021013830 A1 | 1/2021 |
| WO | 2021013832 A1 | 1/2021 |
| WO | 2021013833 A1 | 1/2021 |

OTHER PUBLICATIONS

Kihara et al. Exp Cell Res. May 1, 2015; 333(2): 171-177.*
Zulfikar et al. Clinical Pharmacology: Advances and Applications 2020:12 97-108.*
Castagna, Diana et al. "Development of Autotaxin Inhibitors: An Overview of the Patent and Primary Literature" (2016) Journal of Medicinal Chemistry, 59, 5604-5621.
Desroy, Nicholas et al. "Discovery of 2-[[2-Ethyl-6-[4-[2-(3-hydroxyazetidin-1-yl)-2-oxoethyl]piperazin-1-yl]-8-methylimidazo[1,2-a]pyridin-3-yl]methylamino]-4-(4-fluoropheynyl)thiazole-5-carbonitrile (GLPG1690), a First-in-Class Autotaxin Inhibitor Undergoing Clinical Evaluation for the Treatment of Idiopathic Pulmonary Fibrosis" (2017) Journal of Medicinal Chemistry, 60: 3580-3590.
International Search Report PCT/EP2019/079231 filed Oct. 25, 2019.
Kuttruff, Christian A. et al. "Discovery of BI-2545: A Novel Autotaxin Inhibitor that Significantly Reduces LPA Levels in Vivo" (2017) ACS Medicinal Chemistry Letters, 8: 1252-1257.

* cited by examiner

*Primary Examiner* — Emily A Bernhardt
(74) *Attorney, Agent, or Firm* — Edouard G. Lebel

(57) ABSTRACT

The present invention relates to novel pyridazines according to formula (I)

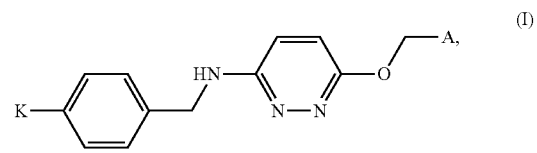

processes for their preparation, pharmaceutical compositions containing them and their use in therapy, particularly in the treatment and/or prevention of diseases and disorders mediated by Autotaxin.

31 Claims, No Drawings

PYRIDAZINES

FIELD OF THE INVENTION

The present invention relates to novel pyridazines, processes for their preparation, pharmaceutical compositions containing them and their use in therapy, particularly in the treatment and/or prevention of diseases and disorders mediated by Autotaxin.

BACKGROUND OF THE INVENTION

Autotaxin (ATX; ENPP2) is a secreted enzyme responsible for hydrolysing lysophosphatidylcholine (LPC) to the bioactive lipid lysophosphatidic acid (LPA) through its lysophospholipase D activity. In turn, LPA exerts its effects by interacting with six GPCRs (LPA Receptors 1-6, LPAR1-6) (Houben A J, 2011). ATX-LPA signalling has been implicated for example in angiogenesis, chronic inflammation, autoimmune diseases, fibrotic diseases, cancer progression and tumor metastasis. For example, LPA, acting on LPAR1, induces lung fibroblast migration, proliferation and differentiation; modulates epithelial and endothelial barrier function; and promotes lung epithelial cell apoptosis (Budd, 2013).

ATX inhibition, LPAR1 gene deletion and selective LPAR1 antagonists have been shown to be effective in pre-clinical models of fibrosis of the lung and skin (Tager A M, 2008; Swaney J, 2010, Casetelino F V, 2016).

In Idiopathic Pulmonary Fibrosis (IPF) patients, LPA levels in bronchoalveolar lavage fluid are increased (Tager et al., 2008, Nat. Med.) and increased concentrations of ATX were detected in human fibrotic lung tissue. (Oikonomou et al., 2012, AJRCMB). LPA levels are elevated in the exhaled breath condensate of IPF subjects (Montesi et al., 2014_BMCPM), and LPC is increased 2-fold in serum of stable IPF patients (Rindlisbacher et al., 2018, Resp. Res.).

Therefore, increased ATX levels and/or increased levels of LPA, altered LPA receptor expression, and altered responses to LPA may affect a number of pathophysiological conditions related to ATX-LPA signaling.

Interstitial Lung Diseases (ILDs) are characterized by inflammation and fibrosis of the interstitium, the tissue and space between the air sacs of the lung (du Bois, Nat. Rev. Drug Discov. 2010, 9, 129-140). An ILD may occur when an injury to the lungs triggers an abnormal healing response. ILDs thus also include Progressive Fibrosing Interstitial Lung Diseases (PFILDs) wherein the response to lung injury becomes progressive, self-sustaining and independent of the original clinical association or trigger. The most prominent PFILDs are Idiopathic Pulmonary Fibrosis (IPF) and Systemic Sclerosis-ILD (SSc-ILD).

IPF is a chronic fibrotic irreversible and ultimately fatal lung disease characterized by a progressive fibrosis in the interstitium in the lung, leading to a decreasing lung volume and progressive pulmonary insufficiency. IPF is also characterized by a specific histopathologic pattern known as usual interstitial pneumonia (UIP) (Raghu et al, Am. J. Respir. Crit. Care Med. 183: 788-824.).

Systemic Sclerosis (SSc) also called scleroderma is an immune-mediated rheumatic disease of complex aetiology. It is a multi-organ, heterogenic disease characterized by extensive fibrosis, vasculopathy and autoantibodies against various cellular antigens with high mortality. It is a rare disorder, an orphan disease with high unmet medical need. The early clinical signs of SSc can be varied. Raynaud's phenomenon and gastro-oesophageal reflux are often present early in the disease (Rongioletti F, et al., J Eur Acad Dermatol Venereol 2015; 29: 2399-404). Some patients present with inflammatory skin disease, puffy and swollen fingers, musculoskeletal inflammation, or constitutional manifestations such as fatigue. Excess collagen deposition in the skin of patients makes the skin thick and tough.

In some patients, organ-based manifestations of the disease, like lung fibrosis, pulmonary arterial hypertension, renal failure or gastrointestinal complication is observed. In addition, one of the most common manifestations of immune involvement is the presence of abnormal levels of autoimmune antibodies to the nucleus of one's own cells (anti-nuclear antibodies or ANA) that are seen in nearly everyone with SSc (Guiducci S et al., Isr Med Assoc J 2016; 18: 141-43). ILD and pulmonary arterial hypertension (PAH) are the most frequent causes of death in patients of SSc (Tyndall A J et al. Ann Rheum Dis 2010; 69: 1809-15).

SSc patients are classified into two major disease subsets: diffuse cutaneous systemic sclerosis, and limited cutaneous systemic sclerosis (LeRoy E C, et al., J Rheumatol 1988; 15:202-5). Three clinical features-excessive fibrosis (scarring), vasculopathy, and autoimmunity-appear to underlie the processes that result in the different manifestations that characterize SSc. SSc is currently considered as a manifestation of dysregulated or dysfunctional repair of connective tissue to injury (Denton C P et al., Lancet 2017; 390: 1685-99).

It is therefore desirable to provide potent ATX inhibitors.

ATX inhibitors of various structural classes are reviewed in D. Castagna et al. (J. Med. Chem. 2016, 59, 5604-5621). WO2014/139882 discloses compounds that are inhibitors of ATX, having the generalized structural formula

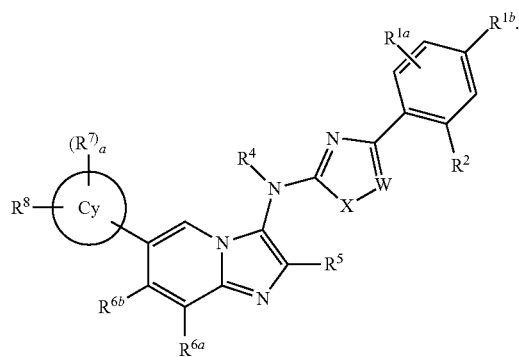

Example 2 therein is further disclosed in N. Desroy, et al (J. Med. Chem. 2017, 60, 3580-3590 as example 11) as a first-in-class ATX inhibitor undergoing clinical evaluation for the treatment of idiopathic pulmonary fibrosis. In C. Kutruff, et al. (ACS Med. Chem. Lett. 2017, 8, 1252-1257) ATX inhibitor BI-2545 (example 19) is disclosed that significantly reduces LPA levels in vivo.

DETAILED DESCRIPTION OF THE INVENTION

The present invention provides novel pyridazines that are surprisingly potent inhibitors of autotaxin (Assay A), further characterized by
 high potency in human whole blood (Assay B), and
 significant reduction in the plasma concentration levels of LPA in vivo over several hours (Assay C).

Compounds of the present invention are useful as agents for the treatment or prevention of diseases or conditions in which ATX activity and/or LPA signalling participates, is involved in the etiology or pathology of the disease, or is otherwise associated with at least one symptom of the disease. ATX-LPA signalling has been implicated for example in angiogenesis, chronic inflammation, autoimmune diseases, fibrotic diseases, cancer progression and tumor metastasis.

Compounds of the invention are superior to those disclosed in the prior art in terms of the combination of the following parameters:

potency as inhibitors of ATX, potency as inhibitors of ATX in human whole blood, reducing the plasma concentration levels of LPA in vivo over several hours ATX is a soluble plasma protein, which is active in heparinized whole blood. Its substrate LPC is highly abundant, its concentration being in the μM range. Therefore, a whole blood assay at physiological substrate concentrations is a highly relevant assay, predictive for the efficacy of ATX inhibitors in vivo.

LPA reduction in vivo is determined by measuring the plasma concentration of LPA after oral dosage of the compounds of the present invention. LPA is a very strong bioactive lipid, which efficiently activates downstream pathways via the LPA-receptors 1-6 in a concentration dependent manner. The pronounced and sustained blockage of the LPA formation via ATX inhibition is assessed by measuring the extent of LPA reduction 8 hours after compound dosage. A high reduction of plasma LPA at 8 h is therefore highly indicative for efficacy and sustained duration of action in vivo as well as sustained target engagement of the LPA receptors.

Compounds of the present invention differ structurally from examples 2 and 12 in WO2014/139882 and example 19 in ACS Med. Chem. Lett. 2017, 8, 1252-1257, in that they contain a central pyridazine core with substituents in the 3- and 6-positions. This structural difference unexpectedly leads to a superior combination of (i) inhibition of ATX, (ii) inhibition of ATX in human whole blood, and (iii) reduced plasma concentration levels of LPA in vivo over several hours.

Consequently, compounds of the present invention demonstrate high in vivo target engagement and can be expected to have higher efficacy in humans.

The present invention provides novel compounds according to formula (I)

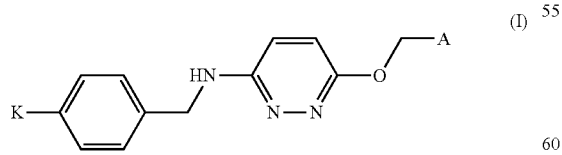

(I)

wherein

A is selected from the group consisting of phenyl and pyridyl, optionally substituted with one or two members of the group consisting of H, $C_{1-4}$-haloalkyl-O—, NC—, F, Cl, Br, and $C_{1-4}$-alkyl-O—;

K is selected from the group consisting of

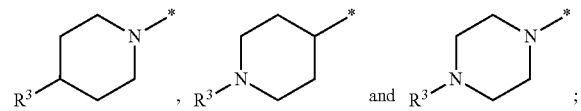

$R^3$ is selected from the group consisting of $R^4(O)C$—;
$R^4$ is $C_{1-6}$-alkyl.

Another embodiment of the present invention relates to a compound of formula I, wherein A is selected from the group consisting of phenyl and pyridyl, optionally substituted with one or two members of the group consisting of H, $F_3CO$—, NC—, F, Cl, Br, and $H_3CO$—; and substituent K is defined as in any of the preceding embodiments.

Another embodiment of the present invention relates to a compound of formula I, wherein A is phenyl, optionally substituted with one or two members of the group consisting of H, $F_3CO$—, NC—, F, Cl, Br, and $H_3CO$—; and substituent K is defined as in any of the preceding embodiments.

Another embodiment of the present invention relates to a compound of formula I, wherein A is pyridyl, optionally substituted with one or two members of the group consisting of H, $F_3CO$—, NC—, F, Cl, Br, and $H_3CO$—; and substituent K is defined as in any of the preceding embodiments.

Preferred is a compound of formula (I) according to the present invention, wherein A is selected from the group consisting of

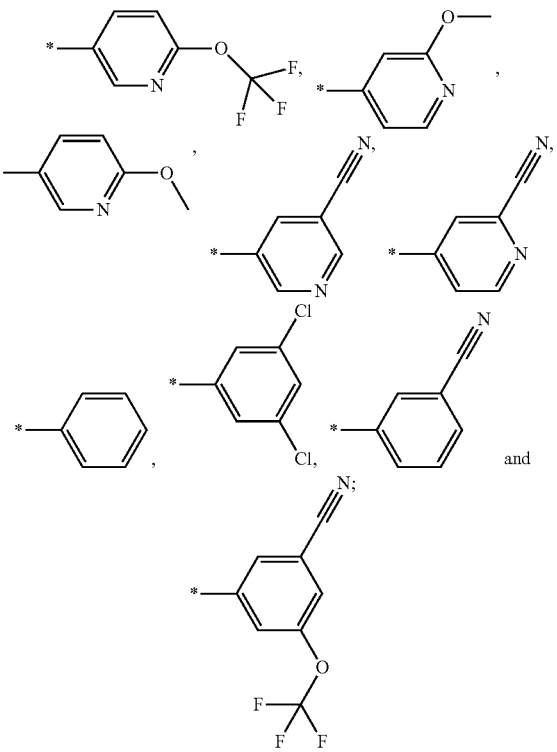

and substituent K is defined as in any of the preceding embodiments.

Particularly preferred is a compound of formula (I) according to the present invention, wherein A is selected from the group consisting of

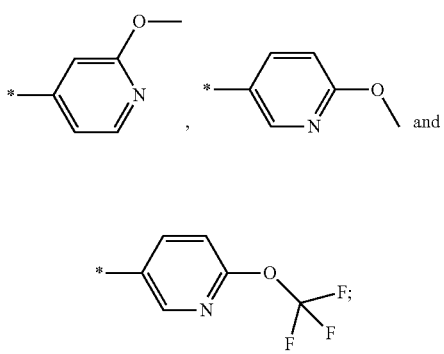

and substituent K is defined as in any of the preceding embodiments.

Preferred is a compound of formula (I) according to the present invention, wherein K is selected from the group consisting of

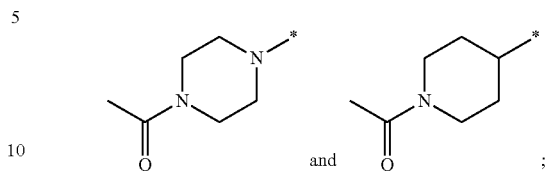

and substituent A is defined as in any of the preceding embodiments.

Particularly preferred is a compound of formula (I) according to the present invention, selected from the group consisting of

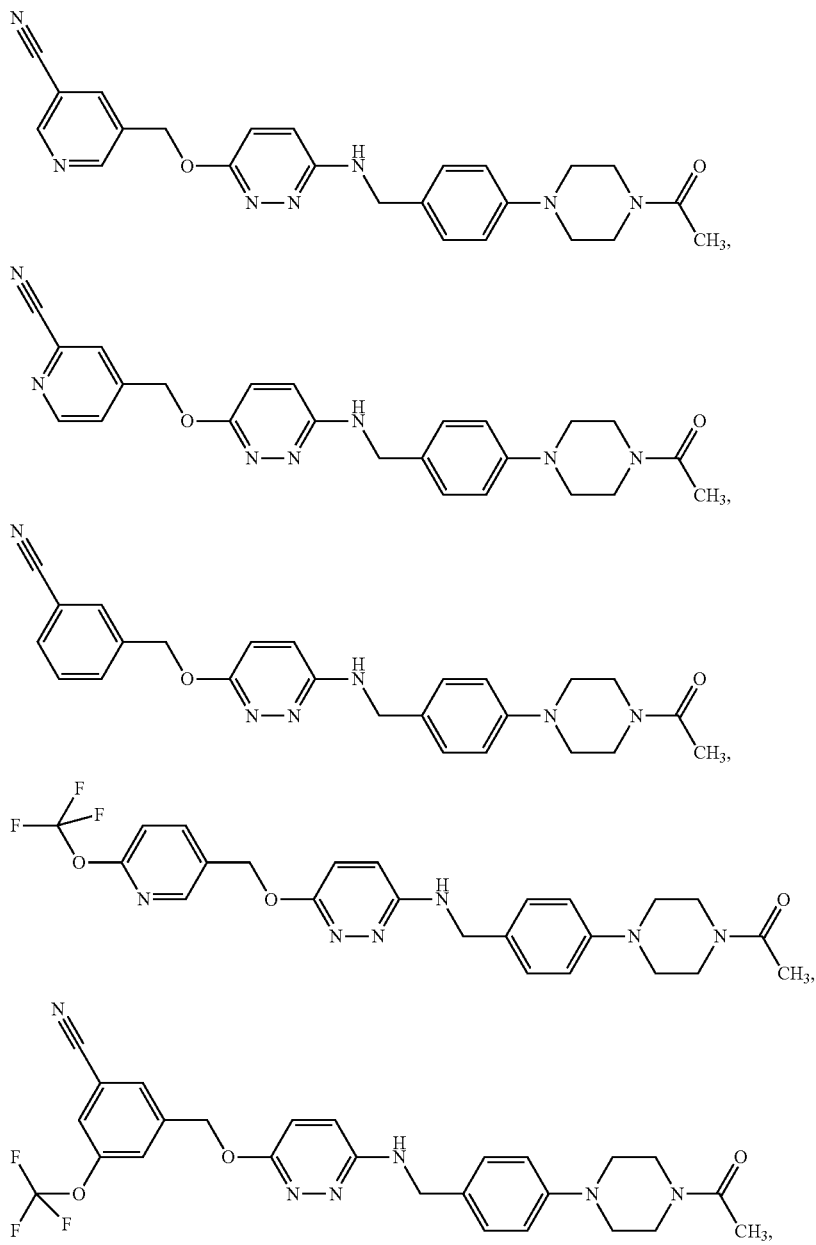

-continued

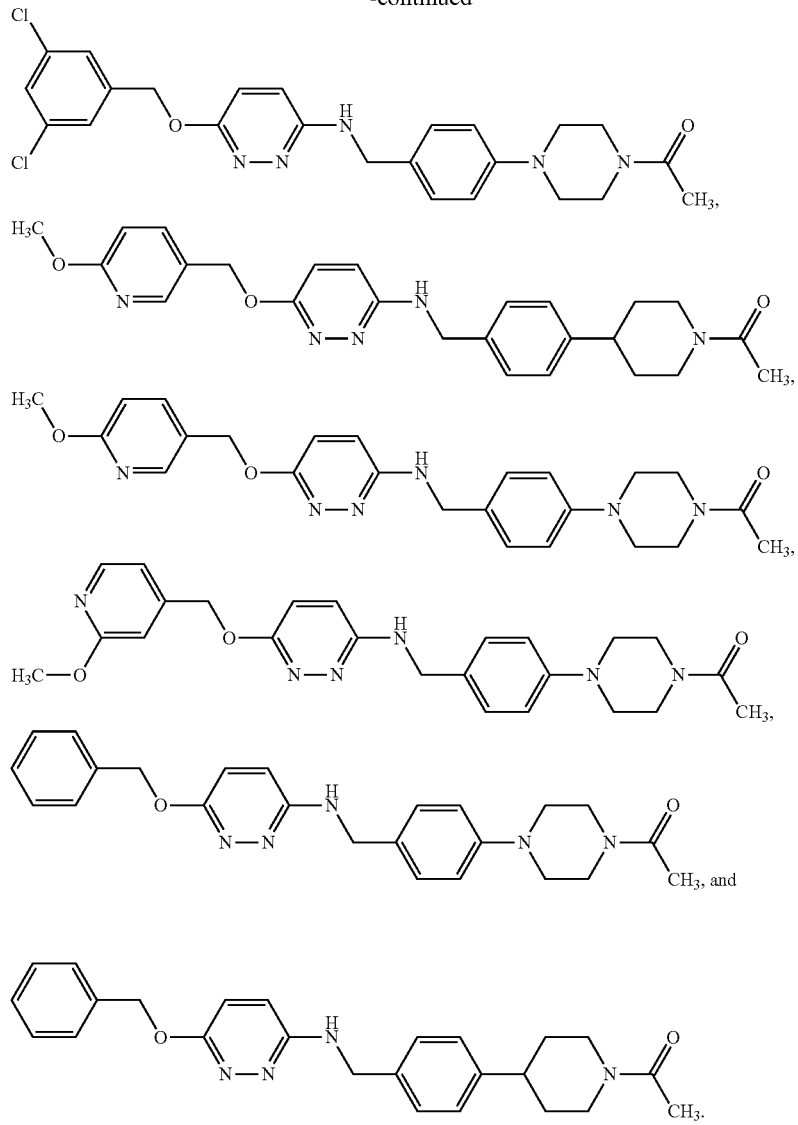

A further embodiment relates to a salt, or particularly a pharmaceutically acceptable salt, of a compound of formula (I) according to the present invention.

A further embodiment relates to a compound of formula (I) according to the present invention, for use as a medicament.

A further embodiment relates to pharmaceutical composition comprising at least one compound of formula (I) according to the present invention and one or more pharmaceutically acceptable excipients.

Used Terms and Definitions

Terms not specifically defined herein should be given the meanings that would be given to them by one of skill in the art in light of the disclosure and the context. As used in the specification, however, unless specified to the contrary, the following terms have the meaning indicated and the following conventions are adhered to.

In the groups, radicals, or moieties defined below, the number of carbon atoms is often specified preceding the group, for example, $C_{1-6}$-alkyl means an alkyl group or radical having 1 to 6 carbon atoms. In general in groups like HO, $H_2N$, (O)S, $(O)_2S$, NC (cyano), HOOC, $F_3C$ or the like, the skilled artisan can see the radical attachment point(s) to the molecule from the free valences of the group itself. For combined groups comprising two or more subgroups, the last named subgroup is the radical attachment point, for example, the substituent "aryl-$C_{1-3}$-alkyl" means an aryl group which is bound to a $C_{1-3}$-alkyl-group, the latter of which is bound to the core or to the group to which the substituent is attached.

In case a compound of the present invention is depicted in form of a chemical name and as a formula in case of any discrepancy the formula shall prevail. An asterisk is may be used in sub-formulas to indicate the bond which is connected to the core molecule as defined.

The numeration of the atoms of a substituent starts with the atom which is closest to the core or to the group to which the substituent is attached.

For example, the term "3-carboxypropyl-group" represents the following substituent:

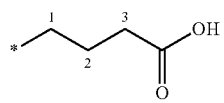

wherein the carboxy group is attached to the third carbon atom of the propyl group. The terms "1-methylpropyl-", "2,2-dimethylpropyl-" or "cyclopropylmethyl-" group represent the following groups:

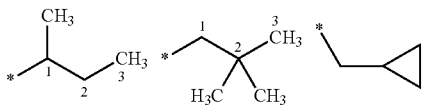

The asterisk may be used in sub-formulas to indicate the bond which is connected to the core molecule as defined.

The term "$C_{1-n}$-alkyl", wherein n is an integer selected from 2, 3, 4, 5 or 6, preferably 4 or 6, either alone or in combination with another radical denotes an acyclic, saturated, branched or linear hydrocarbon radical with 1 to n C atoms. For example the term $C_{1-5}$-alkyl embraces the radicals H$_3$C—, H$_3$C—CH$_2$—, H$_3$C—CH$_2$—CH$_2$—, H$_3$C—CH(CH$_3$)—, H$_3$C—CH$_2$—CH$_2$—CH$_2$—, H$_3$C—CH$_2$—CH(CH$_3$)—, H$_3$C—CH(CH$_3$)—CH$_2$—, H$_3$C—C(CH$_3$)$_2$—, H$_3$C—CH$_2$—CH$_2$—CH$_2$—CH$_2$—, H$_3$C—CH$_2$—CH$_2$—CH(CH$_3$)—, H$_3$C—CH$_2$—CH(CH$_3$)—CH$_2$—, H$_3$C—CH(CH$_3$)—CH$_2$—CH$_2$—, H$_3$C—CH$_2$—C(CH$_3$)$_2$—, H$_3$C—C(CH$_3$)$_2$—CH$_2$—, H$_3$C—CH(CH$_3$)—CH(CH$_3$)— and H$_3$C—CH$_2$—CH(CH$_2$CH$_3$)—.

The term "halogen" denotes chlorine, bromine, iodine, and fluorine. By the term "halo" added to an "alkyl", "alkylene" or "cycloalkyl" group (saturated or unsaturated) is such a alkyl or cycloalkyl group wherein one or more hydrogen atoms are replaced by a halogen atom selected from among fluorine, chlorine or bromine, preferably fluorine and chlorine, particularly preferred is fluorine. Examples include: H$_2$FC—, HF$_2$C—, F$_3$C—.

The term phenyl refers to the radical of the following ring

The term pyridinyl refers to the radical of the following ring

The term pyridazine refers to the following ring

Unless specifically indicated, throughout the specification and the appended claims, a given chemical formula or name shall encompass tautomers and all stereo, optical and geometrical isomers (e.g. enantiomers, diastereomers, E/Z isomers, etc.) and racemates thereof as well as mixtures in different proportions of the separate enantiomers, mixtures of diastereomers, or mixtures of any of the foregoing forms where such isomers and enantiomers exist, as well as salts, including pharmaceutically acceptable salts thereof and solvates thereof such as for instance hydrates including solvates of the free compounds or solvates of a salt of the compound.

In general, substantially pure stereoisomers can be obtained according to synthetic principles known to a person skilled in the field, e.g. by separation of corresponding mixtures, by using stereochemically pure starting materials and/or by stereoselective synthesis. It is known in the art how to prepare optically active forms, such as by resolution of racemic forms or by synthesis, e.g. starting from optically active starting materials and/or by using chiral reagents.

Enantiomerically pure compounds of the present invention or intermediates may be prepared via asymmetric synthesis, for example by preparation and subsequent separation of appropriate diastereomeric compounds or intermediates which can be separated by known methods (e.g. by chromatographic separation or crystallization) and/or by using chiral reagents, such as chiral starting materials, chiral catalysts or chiral auxiliaries.

Further, it is known to the person skilled in the art how to prepare enantiomerically pure compounds from the corresponding racemic mixtures, such as by chromatographic separation of the corresponding racemic mixtures on chiral stationary phases; or by resolution of a racemic mixture using an appropriate resolving agent, e.g. by means of diastereomeric salt formation of the racemic compound with optically active acids or bases, subsequent resolution of the salts and release of the desired compound from the salt; or by derivatization of the corresponding racemic compounds with optically active chiral auxiliary reagents, subsequent diastereomer separation and removal of the chiral auxiliary group; or by kinetic resolution of a racemate (e.g. by enzymatic resolution); by enantioselective crystallization from a conglomerate of enantiomorphous crystals under suitable conditions; or by (fractional) crystallization from a suitable solvent in the presence of an optically active chiral auxiliary.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, and commensurate with a reasonable benefit/risk ratio.

As used herein, "pharmaceutically acceptable salt" refers to derivatives of the disclosed compounds wherein the parent compound forms a salt or a complex with an acid or a base.

Examples of acids forming a pharmaceutically acceptable salt with a parent compound containing a basic moiety include mineral or organic acids such as benzenesulfonic acid, benzoic acid, citric acid, ethanesulfonic acid, fumaric acid, gentisic acid, hydrobromic acid, hydrochloric acid, maleic acid, malic acid, malonic acid, mandelic acid, methanesulfonic acid, 4-methyl-benzenesulfonic acid, phosphoric acid, salicylic acid, succinic acid, sulfuric acid and tartaric acid.

Examples for cations and bases forming a pharmaceutically acceptable salt with a parent compound containing an acidic moiety include Na$^+$, K$^+$, Ca$^{2+}$, Mg$^{2+}$, NH$_4^+$, L-arginine, 2,2'-iminobisethanol, L-lysine, N-methyl-D-glucamine or tris(hydroxymethyl)-aminomethane.

The pharmaceutically acceptable salts of the present invention can be synthesized from the parent compound which contains a basic or acidic moiety by conventional chemical methods. Generally, such salts can be prepared by reacting the free acid or base forms of these compounds with a sufficient amount of the appropriate base or acid in water or in an organic diluent like ether, ethyl acetate, ethanol, isopropanol, or acetonitrile, or a mixture thereof.

Salts of other acids than those mentioned above which for example are useful for purifying or isolating the compounds of the present invention (e.g. trifluoroacetate salts,) also comprise a part of the present invention.

Biological Assays

The biological activity of compounds was determined by the following methods:

Assay A: Biochemical ATX Assay 5 nM recombinant ATX (Cayman Chemicals) was supplemented to 50 mM Tris buffer (pH 8.0) containing 3 mM KCl, 1 mM CaCl2, 1 mM MgCl2 0.14 mM NaCl, and 0.1% bovine serum albumin. Test compounds were dissolved in DMSO and tested in the range of 0.1 nM to 10 µM. The enzymatic reaction (22.5 µL) was started by addition of 2.5 µL 10 µM 18:1 LPC (Avanti Lipids, Alabaster, Ala., USA). After 2-h incubation at room temperature, the reaction was stopped by addition of 20 µL water containing 500 nM 20:4 LPA as internal standard and 100 µL 1-butanol for extracting LPA. Subsequently, the plates were centrifuged at 4000 rpm, 4° C., for 2 min. The resultant upper butanol phase was directly used for injection at a RapidFire system (Agilent).

The RapidFire autosampler was coupled to a binary pump (Agilent 1290) and a Triple Quad 6500 (ABSciex, Toronto, Canada). This system was equipped with a 10-µL loop, 5 µL Waters Atlantis HILIC cartridge (Waters, Elstree, UK), 90% acetonitrile containing 10 mM ammonium acetate as eluent A and 40% acetonitrile containing 10 mM ammoniumacetate as eluent B. For details see (Bretschneider et al., SLAS Discovery, 2017). 1 The MS was operated in negative mode with a source temperature of 550° C., curtain gas=35, gas 1=65, and gas 2=80. The following transitions and MS parameters (DP: declustering potential and CE: collision energy) for the respective LPAs were determined: 18:1 LPA at 435.2/152.8, DP=−40, CE=−28 and 20:4 LPA at 457.2/152.8, DP=−100, CE=−27).

The formation of 18:1 LPA was monitored and evaluated as ratio to 20:4 LPA.

TABLE 1

Biological data for compounds for the invention as obtained in Assay A

| Example | Human ATX LPA IC$_{50}$ [nM] |
|---|---|
| 1.1 | 6 |
| 1.2 | 2 |
| 1.3 | 5 |
| 1.4 | 4 |
| 1.5 | 4 |
| 1.6 | 5 |
| 2.1 | 3 |
| 2.2 | 3 |
| 2.3 | 8 |
| 2.4 | 3 |
| 2.5 | 4 |

TABLE 2

Biological data for prior art compounds (examples 2 and 12 in WO2014/139882) as obtained in Assay A.

| Example in WO2014/139882 | Human ATX LPA IC$_{50}$ [nM] |
|---|---|
| 2 | 5 |
| 12 | 2 |

TABLE 3

Biological data for prior art compounds (example 19 in ACS Med. Chem. Lett. 2017, 8, 1252-1257) as obtained in Assay A.

| Example in ACS Med. Chem. Lett. 2017, 8, 1252-1257 | Human ATX LPA IC$_{50}$ [nM] |
|---|---|
| 19 | 2.2 |

Assay B: Whole-Blood ATX Assay

45 µL human whole-blood was supplemented with 5 µL of the test compound, dissolved in phosphate-buffered saline (concentration range 0.12 nM-100 µM). This mixture was incubated for 1 h at 37° C. and stopped by addition of 100 µL 40 mM disodium hydrogen phosphate buffer containing 30 mM citric acid (pH 4) and 1 µM 17:0 LPA (internal standard). LPA was extracted by addition of 500 µL 1-butanol, followed by 10-min centrifugation at 4000 rpm, 4° C. From the resultant organic supernatant, a 200 µL aliquot was transferred into a 96-deep-well plate and transferred to the RapidFire-based MS/MS measurement.

The RapidFire autosampler was coupled to a binary pump (Agilent 1290) and a Triple Quad 6500 (ABSciex, Toronto, Canada). This system was equipped with a 10-µL loop, 5-µL Waters Atlantis HILIC cartridge (Waters, Elstree, UK), 90% acetonitrile containing 10 mM ammonium acetate as eluent A and 40% acetonitrile containing 10 mM ammoniumacetate as eluent B. For details see (Bretschneider et al., SLAS Discovery, 2017, 22, 425-432). The MS was operated in negative mode with a source temperature of 550° C., curtain gas=35, gas 1=65, and gas 2=80. The following transitions and MS parameters (DP: declustering potential and CE: collision energy) for the respective LPAs were determined: 18:2 LPA at 433.2/152.8, DP=−150, CE=−27 and 17:0 LPA at 423.5/152.8, DP=−100.

The formation of 18:2 LPA was monitored and evaluated as ratio to 17:0 LPA.

TABLE 4

Biological data for compounds for the invention as obtained in Assay B.

| Example | Human whole blood LPA IC$_{50}$ [nM] |
|---|---|
| 1.1 | 46 |
| 1.2 | 55 |
| 1.3 | 83 |
| 1.4 | 201 |
| 1.5 | 9 |
| 2.1 | 33 |
| 2.2 | 38 |
| 2.3 | 186 |

TABLE 4-continued

Biological data for compounds for the invention as obtained in Assay B.

| Example | Human whole blood LPA IC$_{50}$ [nM] |
|---|---|
| 2.4 | 73 |
| 2.5 | 264 |

TABLE 5

Biological data for prior art compounds (examples 2 and 12 in WO2014/139882) as obtained in Assay B.

| Example in WO2014/139882 | Human whole blood LPA IC$_{50}$ [nM] |
|---|---|
| 2 | 370 |
| 12 | 50 |

TABLE 6

Biological data for prior art compounds (example 19 in ACS Med. Chem. Lett. 2017, 8, 1252-1257) as obtained in Assay B.

| Example in ACS Med. Chem. Lett. 2017, 8, 1252-1257 | Human whole blood LPA IC$_{50}$ [nM] |
|---|---|
| 19 | 29 |

Assay C: In Vivo

The test substance was solubilized in 0.5% natrosol supplemented with 0.015% Tween 80 for oral application to rats at a dose of 5 mg/kg. Blood samples were collected before compound administration and 8 hours post application on ice using EDTA as coagulation agent. Subsequently, plasma was prepared by centrifugation and stored until analysis at −20° C.

LPAs from plasma samples were extracted by using the procedure described by Scherer et al. (Clinical chemistry 2009, 55, 1218-22). 35 µL of heparinized plasma was mixed with 200 µL 40 mM disodium hydrogen phosphate buffer containing 30 mM citric acid (pH 4) and 1 µM 17:0 LPA (internal standard). Subsequently, 500 µL butanol was added and shaken vigorously for 10 min. Samples were centrifuged afterwards at 4000 rpm, 4° C., for 10 min. 500 µL of the organic upper phase was transferred to a fresh 96-deep-well plate and evaporated with a gentle nitrogen flow of 15 psi for 45 min. The resultant residual was dissolved in 100 µL ethanol prior to LC-MS analysis.

LC-MS Method for the Analytic of In Vivo Samples

A Triple Quad 6500 (ABSciex, Toronto, Canada) was equipped with an Agilent 1290 LC system (Agilent, Santa Clara, Calif.) a CTC autosampler and an Atlantis 50×2.1-mm, 3-µm HILIC LC column (Waters, Elstree, UK). Eluent A contained 0.2% formic acid and 50 mM ammonium formate in water, whereas eluent B consisted of 0.2% formic acid in acetonitrile. The LC gradient started from 95% solvent B and decreased within 1.5 min to 75% and within 0.2 min to 50% solvent B, with a further increase in the flow rate from 500 to 700 µL·min$^{-1}$. At 1.8 min, solvent B was set back to 95% and stayed constant for 0.7 min for re-equilibration of the column. The following LPA species were monitored (DP: declustering potential and CE: collision energy): 16:0 LPA at 409.2/152.8, DP=−150, CE=−28; 18:0 LPA at 437.3/152.8, DP=−60, CE=−28; 18:1 LPA at 435.2/152.8, DP=−40, CE=−28; 18:2 LPA at 433.2/152.8, DP=−150, CE=−28; 20:4 LPA at 457.2/152.8, DP=−100, CE=−29 and 17:0 LPA at 423.5/152.8, DP=−100, CE=−36. LPA depletion in percent was calculated based on the baseline LPA levels before test compound application. The sum of LPA refers to the species 16:0; 18:0; 18:1; 18:2 and 20:4 Table 7: Biological data for compounds for the invention as obtained in Assay C.

TABLE 7

Biological data for compounds for the invention as obtained in Assay C.

| Example | LPA reduction at 8 h [%] |
|---|---|
| 1.4 | 95.7 |
| 2.1 | 98.3 |

TABLE 8

Biological data for prior art compounds (examples 2 and 12 in WO2014/139882) as obtained in Assay C.

| Example | LPA reduction at 8 h [%] |
|---|---|
| 2 | 58.1 |
| 12 | 60.3 |

TABLE 9

Biological data for prior art compound (example 19 in ACS Med. Chem. Lett. 2017, 8, 1252-1257) as obtained in Assay C.

| Example | LPA reduction at 8 h [%] |
|---|---|
| 19 | 40.7 |

Method of Treatment

The present invention is directed to compounds of general formula (I) which are useful in the prevention and/or treatment of a disease and/or condition associated with or modulated by ATX and/or the biological activity of LPA, including but not limited to the treatment and/or prevention of inflammatory conditions, fibrotic diseases, conditions of the respiratory system, renal conditions, liver conditions, vascular and cardiovascular conditions, cancer, ocular conditions, metabolic conditions, cholestatic and other forms of chronic pruritus and acute and chronic organ transplant rejection and conditions of the nervous system.

The compounds of general formula (I) are useful for the prevention and/or treatment of inflammatory conditions including, but not limited to Sjögren's syndrome, arthritis, osteoarthritis, multiple sclerosis, systemic lupus erythematousus, inflammatory bowel disease, inflammatory airways diseases such as chronic obstructive pulmonary disease (COPD) and chronic asthma; fibrotic diseases including, but not limited to interstitial lung diseases (ILDs) including Progressive Fibrosing Interstitial Lung Diseases (PFILDs) such as idiopathic pulmonary fibrosis (IPF), and SSC-ILD, familial interstitial lung disease myocardial and vascular fibrosis, renal fibrosis, liver fibrosis, pulmonary fibrosis, skin fibrosis, collagen vascular disease including Systemic Sclerosis (SSc) and encapsulating peritonitis; conditions of the respiratory system including, but not limited to diffuse parenchymal lung diseases of different etiologies including iatrogenic drug-induced fibrosis, occupational and/or environmental induced fibrosis, systemic diseases and vasculitides, granulomatous diseases (sarcoidosis, hypersensitivity pneumonia), renal conditions including, but not limited to acute kidney injury and chronic renal disease with and without proteinuria including End-Stage Renal Disease (ESRD, focal segmental glomerular sclerosis, IgA nephropathy, vasculitides/systemic diseases as well as acute and chronic kidney transplant rejection; liver conditions including, but not limited to liver cirrhosis, hepatic congestion, cholestatic liver disease including pruritus, primary biliary cholangitis, non-alcoholic steatohepatitis and acute and chronic liver transplant rejection; vascular conditions including, but not limited to atherosclerosis, thrombotic vascular disease as well as thrombotic microangiopathies, proliferative arteriopathy (such as swollen myointimal cells surrounded by mucinous extracellular matrix and nodular thickening), endothelial dysfunction; cardiovascular conditions including, but not limited to acute coronary syndrome, coronary heart disease, myocardial infarction, arterial and pulmonary hypertension, cardiac arrhythmia such as atrial fibrillation, stroke and other vascular damage; cancer and cancer metastasis including, but not limited to breast cancer, ovarian cancer, lung cancer, prostate cancer, mesothelioma, glioma, hepatic carcinoma, gastrointestinal cancers and progression and metastatic aggressiveness thereof; ocular conditions including, but not limited to proliferative and non-proliferative (diabetic) retinopathy, dry and wet age-related macular degeneration (AMD), macular oedema, central arterial/venous occlusion, traumatic injury, glaucoma; metabolic conditions including, but not limited to obesity, dyslipidaemia and diabetes; conditions of the nervous system including, but not limited to neuropathic pain, Alzheimer's disease, schizophrenia, neuro-inflammation (for example, astrogliosis), peripheral and/or autonomic (diabetic) neuropathies.

Accordingly, the present invention relates to a compound of general formula (I) for use as a medicament.

Furthermore, the present invention relates to the use of a compound of general formula (I) for the treatment and/or prevention of a disease and/or condition associated with or modulated by ATX and/or the biological activity of LPA.

Furthermore, the present invention relates to the use of a compound of general formula (I) for the treatment and/or prevention of a disease and/or condition associated with or modulated by ATX and/or the biological activity of LPA, including but not limited to inflammatory conditions, fibrotic diseases, conditions of the respiratory system, renal conditions, liver conditions, vascular and cardiovascular conditions, cancer, ocular conditions, metabolic conditions, cholestatic and other forms of chronic pruritus and acute and chronic organ transplant rejection and conditions of the nervous system.

Furthermore, the present invention relates to the use of a compound of general formula (I) for the treatment and/or prevention of inflammatory conditions including, but not limited to Sjögren's syndrome, arthritis, osteoarthritis, multiple sclerosis, systemic lupus erythematousus, inflammatory bowel disease, inflammatory airways diseases such as chronic obstructive pulmonary disease (COPD) and chronic asthma; fibrotic diseases including, but not limited to interstitial lung diseases (ILDs) including Progressive Fibrosing Interstitial Lung Diseases (PFILDs) such as idiopathic pulmonary fibrosis (IPF), and SSC-ILD, familial interstitial lung disease myocardial and vascular fibrosis, renal fibrosis, liver fibrosis, pulmonary fibrosis, skin fibrosis, collagen vascular disease including Systemic Sclerosis (SSc) and encapsulating peritonitis; conditions of the respiratory system including, but not limited to diffuse parenchymal lung diseases of different etiologies including iatrogenic drug-induced fibrosis, occupational and/or environmental induced fibrosis, systemic diseases and vasculitides, granulomatous diseases (sarcoidosis, hypersensitivity pneumonia), renal conditions including, but not limited to acute kidney injury and chronic renal disease with and without proteinuria including end-stage renal disease (ESRD, focal segmental glomerular sclerosis, IgA nephropathy, vasculitides/systemic diseases as well as acute and chronic kidney transplant rejection; liver conditions including, but not limited to liver cirrhosis, hepatic congestion, cholestatic liver disease including pruritus, primary biliary cholangitis, non-alcoholic steatohepatitis and acute and chronic liver transplant rejection; vascular conditions including, but not limited to atherosclerosis, thrombotic vascular disease as well as thrombotic microangiopathies, proliferative arteriopathy (such as swollen myointimal cells surrounded by mucinous extracellular matrix and nodular thickening), endothelial dysfunction; cardiovascular conditions including, but not limited to acute coronary syndrome, coronary heart disease, myocardial infarction, arterial and pulmonary hypertension, cardiac arrhythmia such as atrial fibrillation, stroke and other vascular damage; cancer and cancer metastasis including, but not limited to breast cancer, ovarian cancer, lung cancer, prostate cancer, mesothelioma, glioma, hepatic carcinoma, gastrointestinal cancers and progression and metastatic aggressiveness thereof; ocular conditions including, but not limited to proliferative and non-proliferative (diabetic) retinopathy, dry and wet age-related macular degeneration (AMD), macular oedema, central arterial/venous occlusion, traumatic injury, glaucoma; metabolic conditions including, but not limited to obesity, dyslipidaemia and diabetes; conditions of the nervous system including, but not limited to neuropathic pain, Alzheimer's disease, schizophrenia, neuro-inflammation (for example, astrogliosis), peripheral and/or autonomic (diabetic) neuropathies.

In a further aspect the present invention relates to a compound of general formula (I) for use in the treatment and/or prevention of above mentioned diseases and conditions.

In a further aspect the present invention relates to the use of a compound of general formula (I) for the preparation of a medicament for the treatment and/or prevention of above mentioned diseases and conditions.

In a further aspect of the present invention the present invention relates to methods for the treatment or prevention of above mentioned diseases and conditions, which method comprises the administration of an effective amount of a compound of general formula (I) to a human being.

Pharmaceutical Compositions

Suitable preparations for administering the compounds of formula (I) will be apparent to those with ordinary skill in the art and include for example tablets, pills, capsules, suppositories, lozenges, troches, solutions, syrups, elixirs, sachets, injectables, inhalatives and powders etc.

Suitable tablets may be obtained, for example, by mixing one or more compounds according to formula I with known excipients, for example inert diluents, carriers, disintegrants, adjuvants, surfactants, binders and/or lubricants.

Combination Therapy

Compounds according to the present invention can be combined with other treatment options known to be used in the art so that at least two active compounds in effective amounts are used to treat an indication for which the present invention is useful at the same time. Although combination therapy preferably includes the administration of two active compounds to the patient at the same time, it is not necessary that the compounds be administered to the patient at the same time, although effective amounts of the individual compounds will be present in the patient at the same time. Compounds according to the present invention may be administered with one or more combination partners as otherwise described herein.

Accordingly, the present invention provides a compound of formula (I) according to any of the preceding embodiments, characterised in that the compound of formula (I) is administered in addition to treatment with one or more anti-inflammatory molecules from the list consisting of IL6 modulators, anti-IL6R modulators and IL13/IL-4 JAKi modulators. According to another aspect, the present invention provides a compound of formula (I) according to any of the preceding embodiments, characterised in that the compound of formula (I) is administered in addition to treatment with one or more anti-fibrotic molecules from the list consisting of CB2 agonists, TGF modulators, FGFR modulators, VEGFR inhibitors, PDGFR inhibitors, FGF modulators, av136 integrin modulators, anti-CTGF antibodies, ROCK2 inhibitors, rhPTX-2 (Pentraxin-2), JNK1 inhibitors, LOXL2 inhibitors, Galectin3 inhibitors, MK2 inhibitors, Wnt pathway inhibitors, TGFR inhibitors, PDE4 modulators and microRNA modulators.

According to another aspect, the present invention provides a compound of formula (I) according to any of the preceding embodiments, characterised in that the compound of formula (I) is administered in addition to nintedanib.

According to another aspect, the present invention provides a compound of formula (I) according to any of the preceding embodiments, characterised in that the compound of formula (I) is administered in addition to pirfenidone.

Preparation

The compounds according to the present invention may be obtained using methods of synthesis which are known to the one skilled in the art and described in the literature of organic synthesis. Preferably the compounds are obtained analogously to the methods of preparation explained more fully hereinafter, in particular as described in the experimental section.

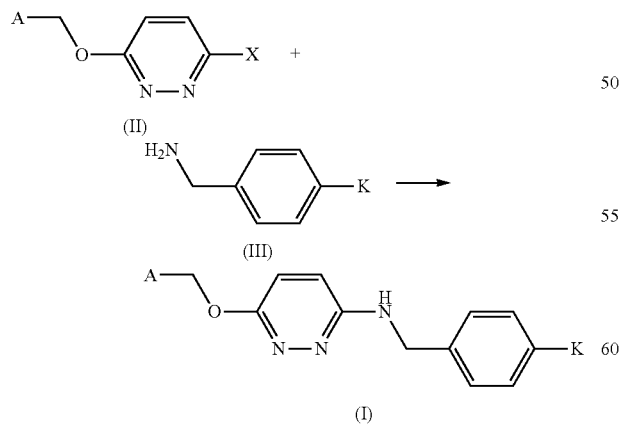

Compounds of general formula (I) may be prepared by palladium-mediated Buchwald reactions or copper-mediated Ullmann reactions of pyridazinyl halogenides or triflates (II) with amines (III) wherein X is a leaving group which for example denotes Cl, Br, I or OTf (triflate).

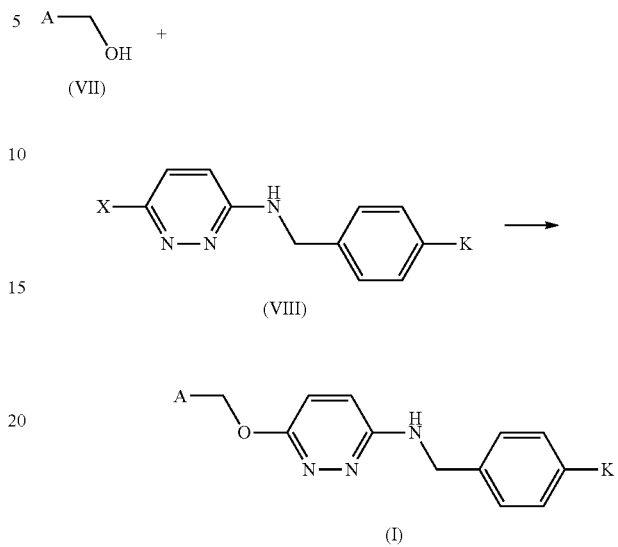

Compounds of general formula (I) may alternatively be prepared by palladium-mediated Buchwald reactions or copper-mediated Ullmann reactions of pyridazinyl halogenides or triflates (VIII) with alcohols (VII) wherein X is a leaving group which for example denotes Cl, Br, I or OTf (triflate).

EXAMPLES

Experimental Part

The Examples that follow are intended to illustrate the present invention without restricting it. The terms "ambient temperature" and "room temperature" are used interchangeably and designate a temperature of about 20° C.

Abbreviations aq. aqueous
ACN acetonitrile
Brett Phos 2-(dicyclohexylphosphino)-3,6-dimethoxy-2'-4'-6'-tri-i-propyl1,1'-biphenyl
Brett Phos Pd G3 methanesulfonato(2-dicyclohexylphosphino-3,6-dimethoxy-2',4',6'-tri-i-propyl-1,1'-biphenyl)(2'-amino-1,1'-biphenyl-2-yl)palladium(II)
DCM dichloro methane
DIPE diisopropyl ether
DIPEA N,N-diisopropylethylamine
DMF N,N-dimethylformamide
DMSO dimethyl sulfoxide
EtOAc ethyl acetate
EtOH ethanol
Et$_2$O diethyl ether
Ex example
Eq equivalent
HCOOH formic acid
MeOH methanol
MgSO$_4$ magnesium sulfate
NaHCO$_3$ sodium bicarbonate
Na$_2$SO$_4$ Sodium sulfate
PE petroleum ether
RT room temperature (about 20° C.)
sat. saturated TEA triethylamine
TFA trifluoroacetic acid
THF tetrahydrofuran Preparation of Starting Compounds Example 1.1

3-(3,5-Dichloro-benzyloxy)-6-iodo-pyridazine

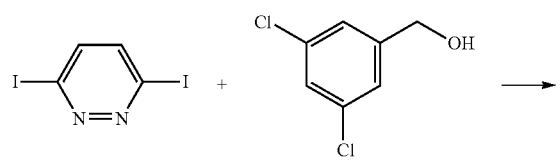

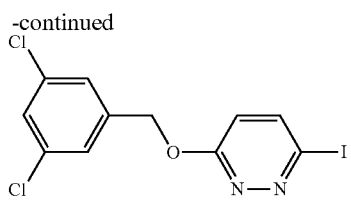

To 1.00 g (3.01 mmol) (3,5-dichloro-phenyl)-methanol in 19 mL THF are added slowly 138 mg (3.16 mmol) sodium hydride in mineral oil (55%) at 0° C. and the mixture is stirred for 30 min at 0° C. 560 mg (3.16 mmol) 3,6-diiodopyridazine are added in portions to the mixture at 0° C. and stirred overnight. The reaction mixture is diluted with water, the precipitate is filtered off, washed with water and dried at 40° C.

$C_{11}H_7Cl_2IN_2O$ (M=380.9 g/mol)
ESI-MS: 381/383/385 [M+H]
$R_f$ (HPLC): 1.20 min (method B)

The following compounds are prepared analogously to example I.1

| Ex. | Starting material | Product structure | ESI-MS | HPLC retention time (method) [min] |
|---|---|---|---|---|
| I.2 | (3-cyano-5-trifluoromethoxy-benzyl alcohol) | | 422 [M + H]⁺ | 1.12 (B) |
| I.3 | (6-methoxy-pyridin-3-yl-methanol) | | 344 [M + H]⁺ | 0.89 (B) |
| I.4 | (2-methoxy-pyridin-4-yl-methanol) | | 344 [M + H]⁺ | 0.86 (B) |
| I.5 | (6-trifluoromethoxy-pyridin-3-yl-methanol) | | 398 [M + H]⁺ | 1.10 (B) |
| I.6 | (benzyl alcohol) | | 313 [M + H]⁺ | analyzed by TLC: $R_f$ = 0.5; silica gel, PE/EtOAc, 5/1 |

| Ex. | Starting material | Product structure | ESI-MS | HPLC retention time (method) [min] |
|---|---|---|---|---|
| I.7 | 3-cyanobenzyl alcohol | | 338 [M + H]⁺ | 0.97 (B) |
| I.8 | 5-(hydroxymethyl)nicotinonitrile | | 339 [M + H]⁺ | 0.86 (A) |
| I.9 | 4-(hydroxymethyl)picolinonitrile | | 339 [M + H]⁺ | 0.84 (C) |

For example 1.2, the precipitate is stirred in MeOH, filtered off and dried at 40° C.

For example 1.8, the precipitate is recrystallised from ACN.

For example 1.9, the precipitate is filtered off and washed with THF. After that, the precipitate is extracted with water and DCM/MeOH, the organic layer is dried over MgSO₄, filtered and the solvent is removed in vacuo. The residue is diluted with tert-butyl methylether, the precipitate is filtered off and dried at 40° C.

Example II.1

4-(1-Acetyl-piperidin-4-yl)-benzonitrile

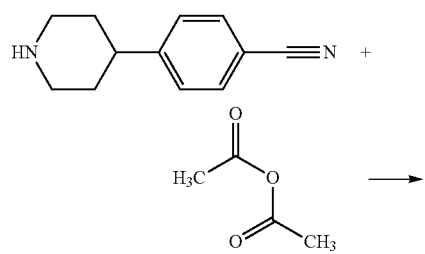

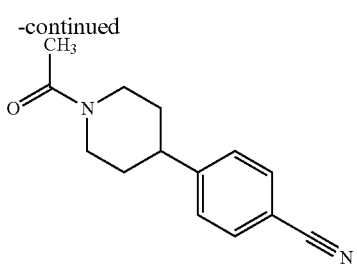

To 2.50 g (13.4 mmol) 4-(4'-cyanophenyl)piperidine in 10.0 mL DCM are added dropwise 1.27 mL (13.4 mmol) acetanhydride. After stirring at RT for 4 h, the reaction mixture is added to water and extracted with DCM. The organic layer is dried over MgSO₄, filtered and the solvent is removed in vacuo. The residue is treated with DIPE, the precipitate is filtered off, washed with DIPE and dried over night at RT.

$C_{14}H_{16}N_2O$ (M=228.3 g/mol)
ESI-MS: 229 [M+H]⁺
$R_t$ (HPLC): 0.87 min (method A)

The following compound is prepared analogously to example II.1

| Ex. | Starting material | Product structure | ESI-MS | HPLC retention time (method) [min] |
|---|---|---|---|---|
| II.2 | 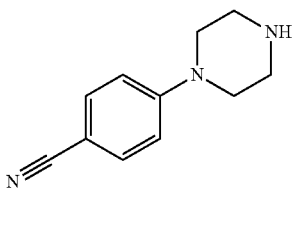 [SMILES: N#Cc1ccc(N2CCNCC2)cc1] | 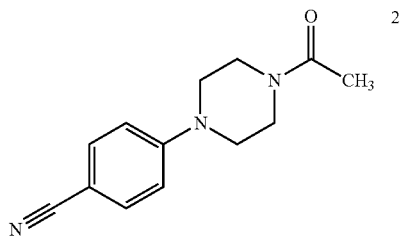 | 230 [M + H]⁺ | 0.83 (B) |

For example II.2, the reaction mixture is extracted with water. The organic layer is neutralised by the addition of aq. Na$_2$CO$_3$ and washed with sat. aq. NaCl, dried over MgSO$_4$, filtered and the solvent is removed in vacuo. The residue is treated with ACN/DIPE, the precipitate is filter off and dried over night at 40° C.

Example X.1

1-[4-(4-Aminomethyl-phenyl)-piperazin-1-yl]-ethanone

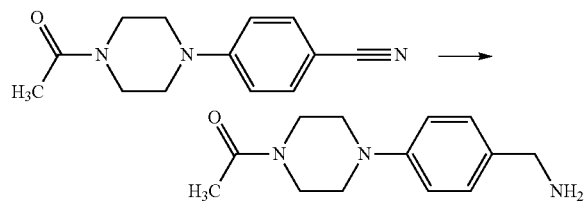

To 950 mg (4.14 mmol) 4-(4-Acetyl-piperazin-1-yl)-benzonitrile (example 11.2) in 10 mL methanolic ammonia are added 90 mg Raney nickel. The reaction mixture is stirred at RT and hydrogen is added (3 bar) over 6 h. The mixture is filtered and the filtrate is concentrated by evaporation. The residue is purified by HPLC.

C$_{13}$H$_{19}$N$_3$O (M=233.3 g/mol)
ESI-MS: 234 [M+H]⁺
R$_t$ (HPLC): 0.56 min (method B)

Example XI.1

1-[4-(4-Aminomethyl-phenyl)-piperidin-1-yl]-ethanone

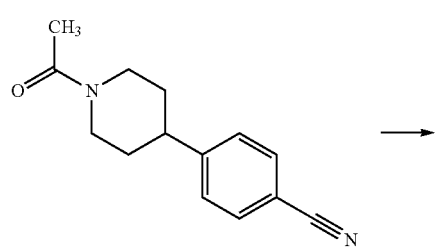

-continued

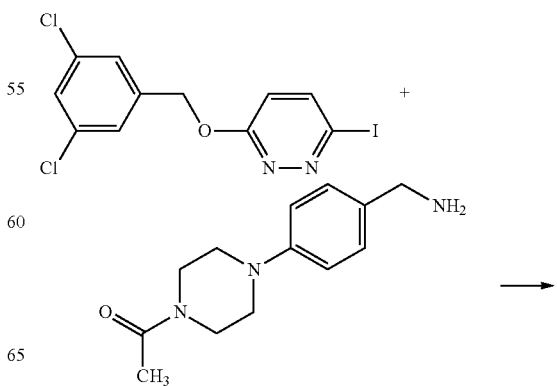

To 890 mg (3.90 mmol) 4-(1-acetyl-piperidin-4-yl)-benzonitrile (example II.1) in 20 mL ethanolic ammonia are added 80.0 mg Raney nickel. The reaction mixture is stirred at 40° C. and hydrogen is added (3 bar) over 18.5 h. The mixture is filtered, the filtrate is concentrated by evaporation and the residue is purified by reverse phase chromatography HPLC (ACN/H$_2$O/NH$_4$OH).

C$_{14}$H$_{20}$N$_2$O (M=232.3 g/mol)
ESI-MS: 233 [M+H]⁺
R$_t$ (HPLC): 0.64 min (method A)

Preparation of Final Compounds

Example 1

Example 1.1

1-[4-(4-{[6-(3,5-Dichloro-benzyloxy)-pyridazin-3-ylamino]-methyl}-phenyl)-piperazin-1-yl]-ethanone -continued

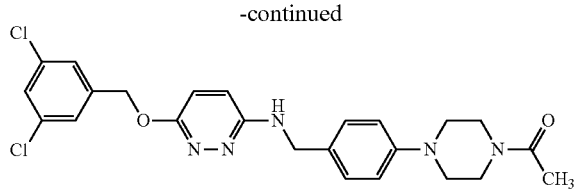

100 mg (0.262 mmol) 3-(3,5-Dichloro-benzyloxy)-6-iodo-pyridazine (example I.1), 67.3 mg (0.289 mmol) 1-[4-(4-aminomethyl-phenyl)-piperazin-1-yl]-ethanone (example X.1), 5.00 mg (26.2 μmol) copper(I) iodide, 8.83 mg (52.5 μmol) 2-(2-methyl-1-oxopropyl)cyclohexanone and 256.5 g (0.787 mmol) cesium carbonate in 1.5 mL DMF are stirred at 90° C. for 4 h under argon. The reaction mixture is filtered and purified by reverse phase chromatography HPLC.

$C_{24}H_{25}Cl_2N_5O_2$ (M=486.4 g/mol)

ESI-MS: 486/488/490 [M+H]

$R_t$ (HPLC): 0.88 min (method B)

The following compounds are prepared according to example 1.1 described above:

| Ex. | Starting materials | | Structure | ESI-MS | HPLC retention time (method) [min] |
|---|---|---|---|---|---|
| 1.2 | I.8 | X.1 | 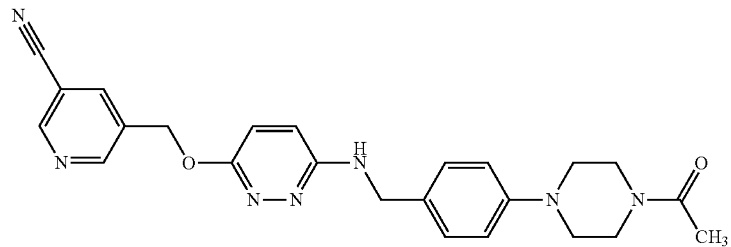 | 444 [M + H]⁺ | 0.58 (G) |
| 1.3 | I.9 | X.1 | 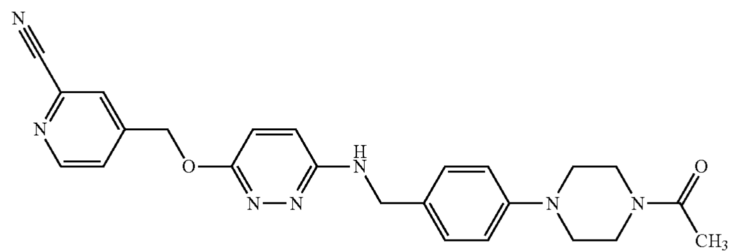 [SMILES: CC(=O)N1CCN(c2ccc(CNc3ccc(OCc4cccc(C#N)c4)nn3)cc2)CC1] | 444 [M + H]⁺ | 0.61 (G) |
| 1.4 | I.7 | X.1 | 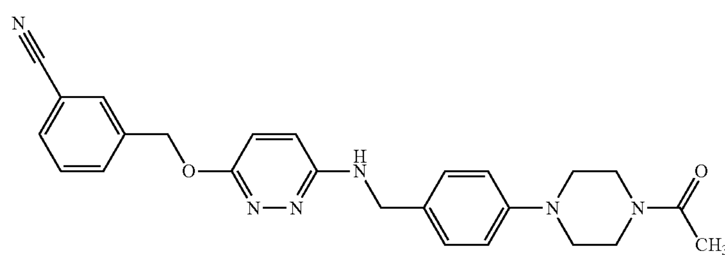 | 443 [M + H]⁺ | 0.69 (G) |
| 1.5 | I.5 | X.1 | 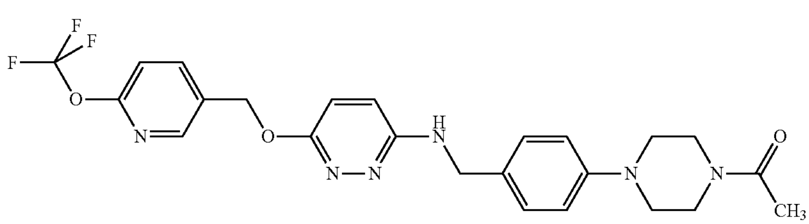 [SMILES: CC(=O)N1CCN(c2ccc(CNc3ccc(OCc4ccc(OC(F)(F)F)nc4)nn3)cc2)CC1] | 503 [M + H]⁺ | 0.81 (H) |

| Ex. | Starting materials | Structure | ESI-MS | HPLC retention time (method) [min] |
|---|---|---|---|---|
| 1.6 | I.2  X.1 | 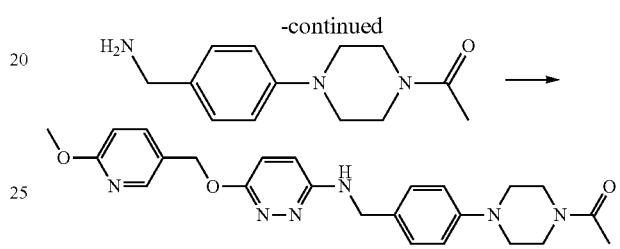 | 527 [M + H]⁺ | 0.87 (H) |

For examples 1.2 and 1.3, 0.25 Eq. copper(I) iodide and 2.50 eq. cesium carbonate are used. For examples 1.2 and 1.3, the reaction conditions are 75° C. overnight. For examples 1.4, 1.5 and 1.6, the reaction conditions are 90° C. overnight.

Example 2

Example 2.1

1-[4-(4-{[6-(6-Methoxy-pyridin-3-ylmethoxy)-pyridazin-3-ylamino]-methyl}-phenyl)-piperazin-1-yl]-ethanone

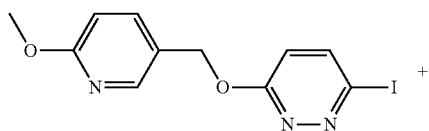

100 mg (0.291 mmol) 3-Iodo-6-(6-methoxy-pyridin-3-ylmethoxy)-pyridazin (example 1.3), 81.5 mg (0.350 mmol) 1-[4-(4-aminomethyl-phenyl)-piperazin-1-yl]-ethanone (example X.1), 26.4 mg (29.1 µmol) Brett Phos Pd G3, 15.6 mg (29.1 µmol) Brett Phos and 84.0 mg (0.874 mmol) sodium tert-butylate in 2.3 mL dioxane are stirred at 60° C. overnight. The reaction mixture is filtered and purified by reverse phase chromatography HPLC.

$C_{24}H_{28}N_6O_3$ (M=448.5 g/mol)
ESI-MS: 449 [M+H]⁺
$R_t$ (HPLC): 0.73 min (method B)

The following compounds are prepared according to example 2.1 described above:

| Ex. | Starting materials | Structure | ESI-MS | HPLC retention time (method) [min] |
|---|---|---|---|---|
| 2.2 | I.3  XI.1 | 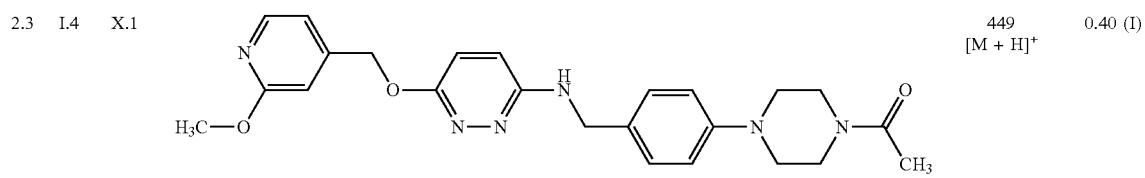 | 448 [M + H]⁺ | 0.70 (G) |
| 2.3 | I.4  X.1 | 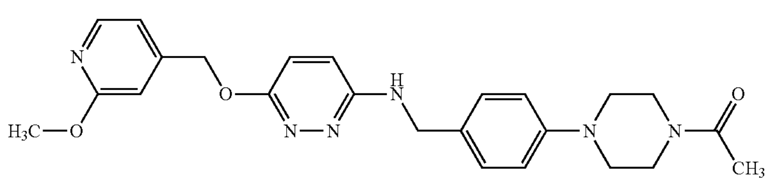 [SMILES: COc1cc(COc2ccc(NCc3ccc(N4CCN(C(C)=O)CC4)cc3)nn2)ccn1] | 449 [M + H]⁺ | 0.40 (I) |

-continued

| Ex. | Starting materials | Structure | ESI-MS | HPLC retention time (method) [min] |
|---|---|---|---|---|
| 2.4 | I.6 X.1 | 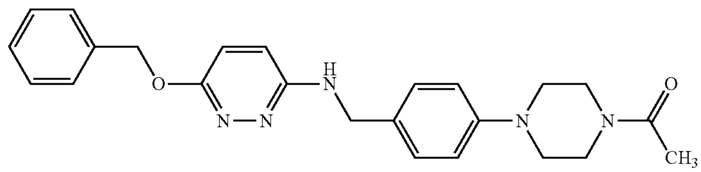 [SMILES: CC(=O)N1CCN(c2ccc(CNc3ccc(OCc4ccccc4)nn3)cc2)CC1] | 418 [M + H]+ | 0.74 (G) |
| 2.5 | I.6 XI.1 | 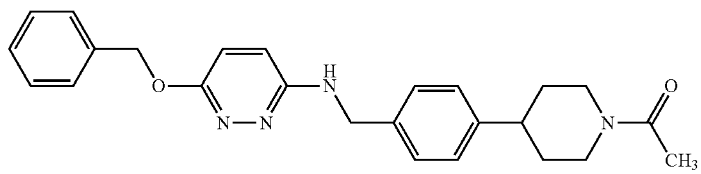 | 417 [M + H]+ | 0.78 (G) |

For examples 2.2 and 2.5, the reaction mixture is added to water and extracted with DCM. The organic layer is washed with water, dried over MgSO$_4$, filtered and the solvent is removed in vacuo. The residue is dissolved in ACN and purified by reverse phase chromatography HPLC. For examples 2.2 and 2.5, the reaction conditions are 70° C. for 120 min. For example 2.3, the reaction conditions are 70° C. for 60 min. For example 2.4, the reaction conditions are 60° C. for 60 min.

Analytical HPLC Methods

Method A

| time (min) | Vol % water (incl. 0.1% TFA) | Vol % ACN | Flow [mL/min] |
|---|---|---|---|
| 0.00 | 97 | 3 | 2.2 |
| 0.20 | 97 | 3 | 2.2 |
| 1.20 | 0 | 100 | 2.2 |
| 1.25 | 0 | 100 | 3.0 |
| 1.40 | 0 | 100 | 3.0 |

Analytical column: Stable Bond (Agilent) 1.8 µm; 3.0×30 mm; column temperature: 60° C.

Method B

| time (min) | Vol % water (incl. 0.1% TFA) | Vol % ACN | Flow [mL/min] |
|---|---|---|---|
| 0.00 | 97 | 3 | 2.2 |
| 0.20 | 97 | 3 | 2.2 |
| 1.20 | 0 | 100 | 2.2 |
| 1.25 | 0 | 100 | 3.0 |
| 1.40 | 0 | 100 | 3.0 |

Analytical column: Sunfire (Waters) 2.5 µm; 3.0×30 mm; column temperature: 60° C.

Method C

| time (min) | Vol % water (incl. 0.1% TFA) | Vol % ACN | Flow [mL/min] |
|---|---|---|---|
| 0.00 | 97 | 3 | 2.2 |
| 0.20 | 97 | 3 | 2.2 |
| 1.20 | 0 | 100 | 2.2 |
| 1.25 | 0 | 100 | 3.0 |
| 1.40 | 0 | 100 | 3.0 |

Analytical column: XBridge C18 (Waters) 2.5 µm; 3.0×30 mm; column temperature: 60° C.

Method G

| time (min) | Vol % water (incl. 0.1% NH$_4$OH) | Vol % ACN | Flow [mL/min] |
|---|---|---|---|
| 0.00 | 95 | 5 | 1.5 |
| 1.30 | 0 | 100 | 1.5 |
| 1.50 | 0 | 100 | 1.5 |
| 1.60 | 95 | 5 | 1.5 |

Analytical column: XBridge C18 (Waters) 2.5 µm; 3.0×30 mm; column temperature: 60° C.

Method H

| time (min) | Vol % water (incl. 0.1% NH$_4$OH) | Vol % ACN | Flow [mL/min] |
|---|---|---|---|
| 0.00 | 95 | 5 | 1.5 |
| 0.30 | 1 | 99 | 1.5 |
| 1.50 | 1 | 99 | 1.5 |
| 1.60 | 95 | 5 | 1.5 |

Analytical column: XBridge C18 (Waters) 3.5 µm; 3.0×30 mm; column temperature: 60° C.

Method I

| time (min) | Vol % water (incl. 0.1% TFA) | Vol % ACN (incl. 0.08% TFA) | Flow [mL/min] |
|---|---|---|---|
| 0.00 | 95 | 5 | 1.5 |
| 1.30 | 0 | 100 | 1.5 |
| 1.50 | 0 | 100 | 1.5 |
| 1.60 | 95 | 5 | 1.5 |

Analytical column: Sunfire C18 (Waters) 2.5 µm; 3.0×30 mm; column temperature: 60° C.

The invention claimed is:

1. A compound according to formula (I)

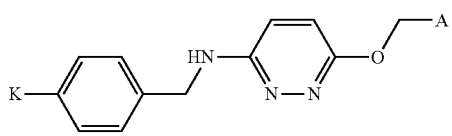

wherein

A is selected from the group consisting of phenyl and pyridyl optionally substituted with one or two members of the group consisting of H, $C_{1-4}$-haloalkyl-O—, NC—, F, Cl, Br, and $C_{1-4}$-alkyl-O—;

K is selected from the group consisting of

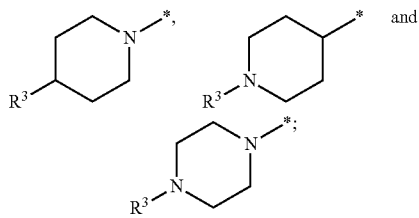

$R^3$ is $R^4(O)C$—;

and;

$R^4$ is $C_{1-6}$-alkyl or a pharmaceutically acceptable salt thereof.

2. The compound of formula (I) according to claim 1, wherein A is selected from the group consisting of phenyl and pyridyl optionally substituted with one or two members of the group consisting of H, $F_3CO$—, NC—, F, Cl, Br, and $H_3CO$—.

3. The compound of formula (I) according to claim 1, wherein A is phenyl, optionally substituted with one or two members of the group consisting of H, $F_3CO$—, NC—, F, Cl, Br, and $H_3CO$—.

4. The compound of formula (I) according to claim 1, wherein A is pyridyl, optionally substituted with one or two members of the group consisting of H, $F_3CO$—, NC—, F, Cl, Br, and $H_3CO$—.

5. The compound of formula (I) according to claim 1, wherein A is selected from the group consisting of

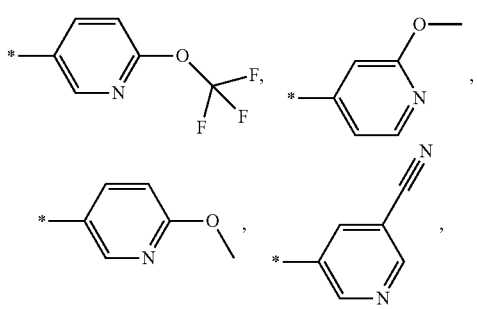

-continued

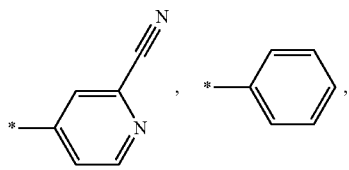

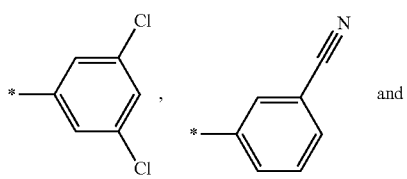

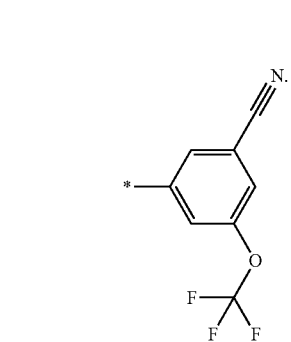

6. The compound of formula (I) according to claim 1, wherein A is selected from the group consisting of

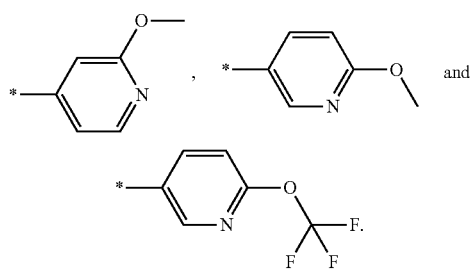

7. The compound of formula (I) according to claim 1, wherein K is selected from the group consisting of

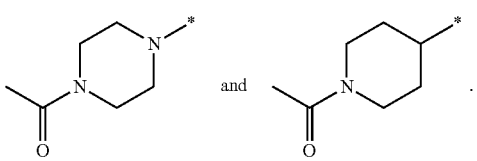

8. The compound of formula (I) according to claim 1, selected from the group consisting of

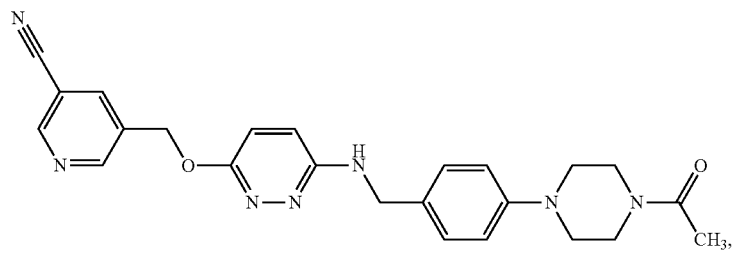
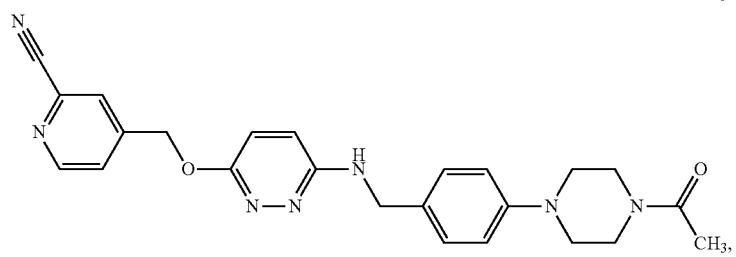
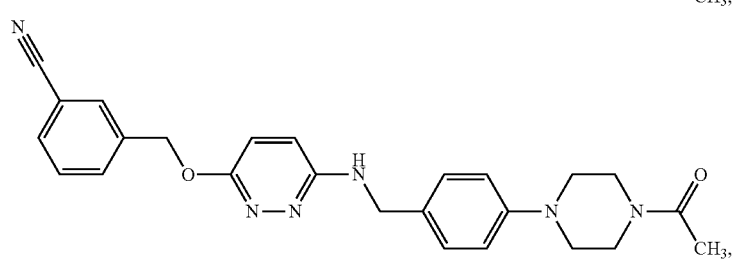
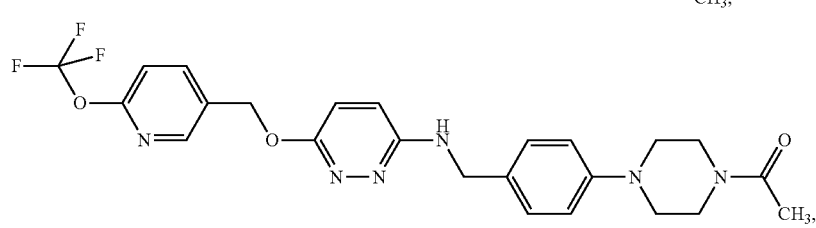
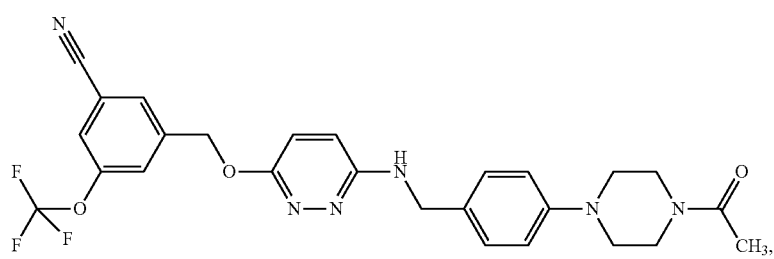
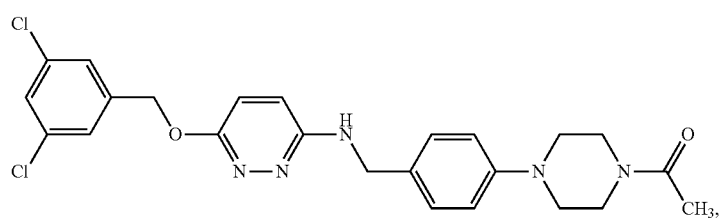
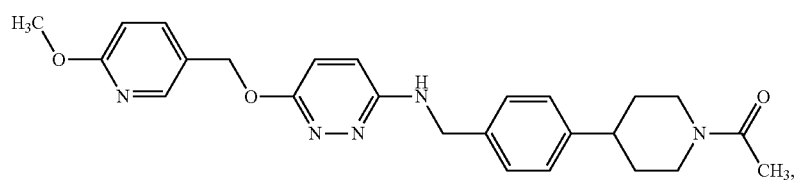

-continued

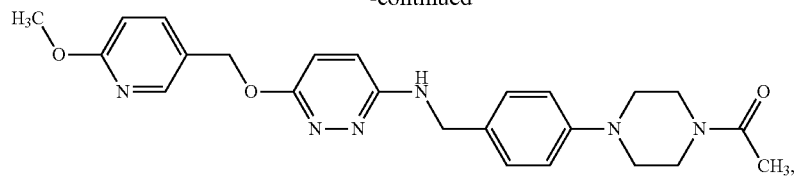

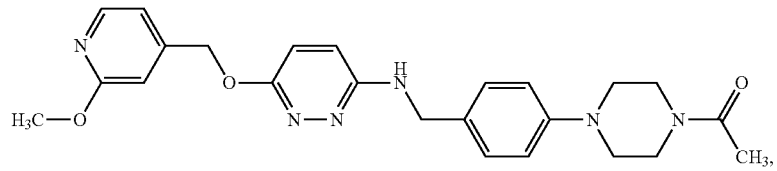

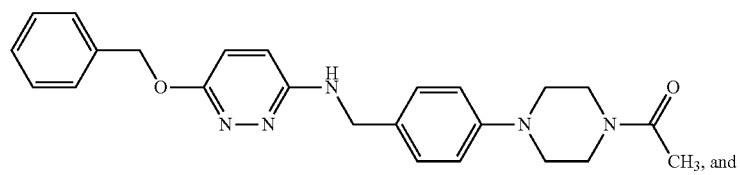

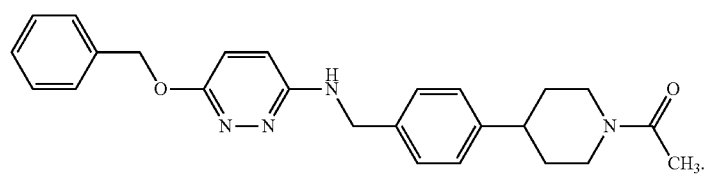

9. A compound of formula (I) according to claim 1.

10. A pharmaceutical composition comprising a compound of formula (I) according to claim 1 and one or more pharmaceutically acceptable excipients.

11. A method for the treatment or prevention of idiopathic lung disease (IPF) and systemic sclerosis (SSc) comprising administering to a patient a compound of formula (I) according to claim 1.

12. Compound of formula

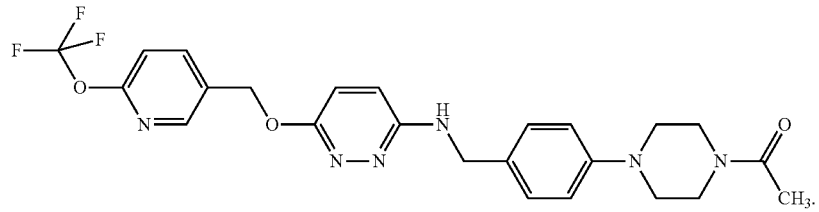 [SMILES: CC(=O)N1CCN(c2ccc(CNc3ccc(OCc4ccc(OC(F)(F)F)nc4)nn3)cc2)CC1]

13. A compound according to claim 12.

14. A pharmaceutical composition comprising a compound according to claim 12 and one or more pharmaceutically acceptable excipients.

15. A method for the treatment of idiopathic lung disease (IPF) and systemic sclerosis (SSc) comprising administering to a patient a compound according to claim 12.

16. Compound of formula

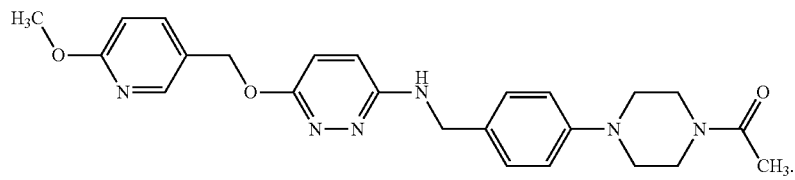

17. A compound according to claim 16.

18. A pharmaceutical composition comprising a compound according to claim 16 and one or more pharmaceutically acceptable excipients.

19. A method for the treatment of idiopathic lung disease (IPF) and systemic sclerosis (SSc) comprising administering to a patient a compound according to claim 16.

20. Compound of formula

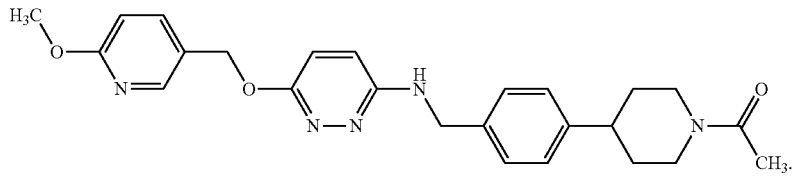

21. A compound according to claim 20.

22. A pharmaceutical composition comprising a compound according to claim 20 and one or more pharmaceutically acceptable excipients.

23. A method for the treatment of idiopathic lung disease (IPF) and systemic sclerosis (SSc) comprising administering to a patient a compound according to claim 20.

24. Compound of formula

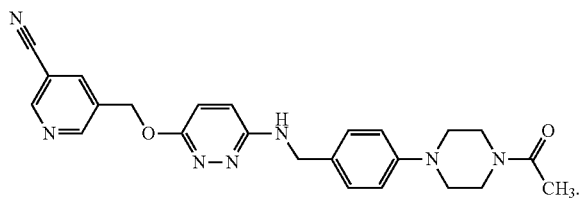 [SMILES: CC(=O)N1CCN(c2ccc(CNc3ccc(OCc4cncc(C#N)c4)nn3)cc2)CC1]

25. A compound according to claim 24.

26. A pharmaceutical composition comprising a compound according to claim 24 and one or more pharmaceutically acceptable excipients.

27. A method for the treatment of idiopathic lung disease (IPF) and systemic sclerosis (SSc) comprising administering to a patient a compound according to claim 24.

28. Compound of formula

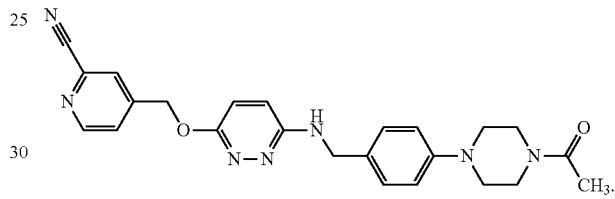

29. A compound according to claim 28.

30. A pharmaceutical composition comprising a compound according to claim 28 and one or more pharmaceutically acceptable excipients.

31. A method for the treatment of idiopathic lung disease (IPF) and systemic sclerosis (SSc) comprising administering to a patient a compound according to claim 28.

* * * * *